United States Patent
Li et al.

(10) Patent No.: US 10,279,077 B2
(45) Date of Patent: May 7, 2019

(54) COLLAGEN-COATED TISSUE-BASED MEMBRANES

(71) Applicant: Collagen Matrix, Inc., Oakland, NJ (US)

(72) Inventors: Shu-Tung Li, Wyckoff, NJ (US); Debbie Yuen, Woodcliff Lake, NJ (US)

(73) Assignee: Collagen Matrix, Inc., Oakland, NJ (US)

(*) Notice: Subject to any disclaimer, the term of this patent is extended or adjusted under 35 U.S.C. 154(b) by 0 days.

(21) Appl. No.: 16/101,907

(22) Filed: Aug. 13, 2018

(65) Prior Publication Data

US 2018/0344897 A1    Dec. 6, 2018

Related U.S. Application Data

(62) Division of application No. 13/408,319, filed on Feb. 29, 2012, now Pat. No. 10,071,184.

(51) Int. Cl.
| | | |
|---|---|---|
| A61L 27/24 | (2006.01) | |
| A61L 27/34 | (2006.01) | |
| A61L 27/36 | (2006.01) | |
| A61L 31/04 | (2006.01) | |
| A61L 31/10 | (2006.01) | |
| A61L 31/14 | (2006.01) | |
| A61L 27/28 | (2006.01) | |

(52) U.S. Cl.
CPC ............ *A61L 27/34* (2013.01); *A61L 27/3604* (2013.01); *A61L 27/3629* (2013.01); *A61L 27/3687* (2013.01); *A61L 31/044* (2013.01); *A61L 31/10* (2013.01); *A61L 31/14* (2013.01); *A61F 2310/00976* (2013.01); *A61F 2310/00982* (2013.01); *A61L 27/24* (2013.01); *A61L 27/28* (2013.01); *A61L 2430/40* (2013.01)

(58) Field of Classification Search
CPC ........ A01N 59/06; A01N 25/06; A01N 59/00; A01N 59/16; A01N 59/20; A01N 25/16; A01N 25/04; A01N 25/34; A61K 2300/00; A61K 36/00; A61K 36/31; A61K 36/185; A61K 36/23; A61K 36/28; A61K 36/286; A61K 36/42; A61K 36/47; A61K 36/48; A61K 36/889; A61K 36/899; A61K 31/167; A61K 31/185; A61K 31/403; A61K 31/436; A61K 31/551; A61K 31/5513; A61K 47/20; A61K 47/44; A61K 8/06; A61K 8/66; A61K 8/922; A61K 9/0014; A61K 9/5047; A61K 9/5078; A61K 2039/507; A61K 2039/54; A61K 2039/55566; A61K 2039/55588; A61K 2800/413; A61K 39/39; A61K 8/02; A61K 8/27; A61K 8/97; A61K 9/0019; A61K 9/107; A61L 2/238; A61L 9/14; A61L 2209/22; A61L 2/23; A61L 2/232; A61L 9/16; A61L 2/16; A61L 2/22; A61L 2202/122; A61L 2202/182; A61L 2/183; A61L 2/186; A61L 2/202; A61L 2/26; A61L 9/014; A61L 9/12; A61L 9/145

See application file for complete search history.

(56) References Cited

U.S. PATENT DOCUMENTS

| | | | |
|---|---|---|---|
| 4,801,299 A | 1/1989 | Brendel et al. | |
| 5,397,353 A | 3/1995 | Oliver et al. | |
| 5,733,337 A | 3/1998 | Carr, Jr. et al. | |
| 5,837,278 A | 11/1998 | Geistlich et al. | |
| 5,993,844 A | 11/1999 | Abraham et al. | |
| 6,277,397 B1* | 8/2001 | Shimizu ............... | A61L 27/24 128/DIG. 8 |
| 6,391,333 B1 | 5/2002 | Li et al. | |
| 6,599,524 B2 | 7/2003 | Li et al. | |
| 6,713,085 B2 | 3/2004 | Geistlich et al. | |
| 6,893,653 B2 | 5/2005 | Abraham et al. | |
| 7,084,082 B1* | 8/2006 | Shimizu ............... | A61L 15/325 424/443 |
| 7,141,072 B2* | 11/2006 | Geistlich ............ | A61F 2/30756 623/23.74 |
| 7,807,192 B2 | 10/2010 | Li et al. | |
| 2004/0048796 A1 | 3/2004 | Hariri et al. | |
| 2005/0186673 A1 | 8/2005 | Geistlich et al. | |
| 2006/0025786 A1 | 2/2006 | Giannetti et al. | |
| 2009/0124540 A1 | 5/2009 | Prestwich et al. | |
| 2011/0270394 A1* | 11/2011 | Herford ............... | A61L 31/044 623/15.12 |
| 2011/0293691 A1 | 12/2011 | Weber et al. | |
| 2012/0010636 A1 | 1/2012 | Boey et al. | |

FOREIGN PATENT DOCUMENTS

| | | |
|---|---|---|
| AU | 2003/292332 B2 | 6/2004 |
| JP | 05260950 A | 10/1993 |
| WO | WO-1995/022301 A1 | 8/1995 |
| WO | WO-1999/019005 A1 | 4/1999 |
| WO | WO-2010/083487 A1 | 7/2010 |

OTHER PUBLICATIONS

Niknejad et al "Properties of the Amniotic Membrane for Potential Use in Tissue Engineering" European Cells and Materials vol. 15, pp. 88-99, 2008.

Reddy et al "A Clinical Study of a Fibrinogen-Based Collagen Fleece for Dural Repair in Neurosurgery" Acta Neurochirurgica vol. 144, pp. 265-169, 2002.

* cited by examiner

*Primary Examiner* — Audrea B Coniglio
(74) *Attorney, Agent, or Firm* — Cesari and McKenna, LLP

(57) ABSTRACT

A collagen-coated tissue based membrane that is smooth on both sides so as to inhibit cell and tissue adhesion. Also disclosed are methods for making a collagen-coated tissue-based membrane.

12 Claims, No Drawings

COLLAGEN-COATED TISSUE-BASED MEMBRANES

CROSS-REFERENCE TO RELATED APPLICATIONS

The present application is a divisional of commonly assigned copending U.S. patent application Ser. No. 13/408,319, which was filed on Feb. 29, 2012. The content of the prior application is hereby incorporated by reference in its entirety.

BACKGROUND

Biocompatible membranes can be prepared by several different methods. In one method, purified collagen fibers extracted from collagen-rich tissues (e.g., tendon and dermis) are used to reconstitute a membrane, as described in U.S. Pat. Nos. 6,391,333; 6,599,524; and 7,807,192. An alternative method relies on the use of a tissue-derived membrane (e.g., pericardium, peritoneum, and small intestine submucosa) as a starting material, as described in U.S. Pat. Nos. 5,837,278 and 5,993,844.

Tissue-derived membranes such as pericardium and peritoneum typically contain two sides. The side that is in contact with internal organs and body fluid is known as the visceral, or serous, layer, while the side that is in contact with the abdominal or heart walls is termed the parietal layer. The visceral layer, which is smooth, does not adhere to adjacent body tissue. By contrast, the parietal layer is integrated with the tissue adjacent to it. The parietal layer must be mechanically separated from the adjacent body wall tissue in order to remove a tissue-based membrane from the body. The parietal layer of a tissue-based membrane torn from the integrated soft tissue of the body wall is covered with fibrous material. This fiber-covered surface of the parietal layer is adhesive, favoring cell adhesion and tissue growth. The fibrous material on the parietal side of membranes isolated from animals can be easily identified under microscopy, such as scanning electron microscopy.

Biocompatible membranes are often used in medical and dental surgeries. At times, it is necessary to use a membrane that is not adhesive on either side so as to avoid any adhesion to the surrounding tissue. For example, a non-adhesive membrane can be used for surgical repair of torn dural membranes, as well as for dental surgery requiring guided tissue repair.

The need exists for a tissue-based biocompatible membrane that can be used in situations where cell adhesion to the membrane is undesirable.

SUMMARY

The main objective of the present invention is to provide the surgical community with a biocompatible tissue-based membrane that is minimally adhesive on both sides for use in tissue repair and regeneration applications.

Thus, one aspect of this invention relates to a tissue-based coated membrane that includes a serous membrane having a fibrous surface coated with a layer of collagen and an uncoated smooth surface such that both the coated fibrous surface and the uncoated smooth surface adhere poorly to cells and tissues. The serous membrane can be, e.g., pericardium, peritoneum, amnion, small intestine submucosa, pleural, or vaginal tunics. In a preferred embodiment, the serous membrane is pericardium or peritoneum. In another preferred embodiment, the fibrous surface of the serous membrane is coated with fiber-forming collagen. The fiber-forming collagen can be type I collagen, type II collagen, type III collagen, or a combination of two or more of these three types.

Another aspect of this invention relates to a method for preparing a biocompatible collagen-coated serous membrane. The method includes a step in which the fibrous side of the serous membrane is scraped to remove adhering fibers. The scraped serous membrane is then treated to remove cells, lipids, and extractable blood and non-collagenous molecules, followed by freeze-drying of the treated serous membrane. The fibrous side of the treated serous membrane is compressed and then coated with a collagen. Finally, the collagen-coated serous membrane is exposed to a crosslinking agent to effect crosslinking. In an embodiment, the serous membrane is rinsed with a dehydrating agent prior to the scraping step to allow for more efficient removal of fibers adhering to the fibrous side of the membrane. The dehydrating agent can be a small organic molecule such as acetone or an alcohol. In another embodiment, the fibrous side of the treated serous membrane is coated with a fiber-forming collagen that can be type I collagen, type II collagen, type III collagen, or a combination thereof. It is preferred that the collagen is type I collagen. The collagen can be coated onto the fibrous side of the treated serous membrane by spraying, brushing, or dipping. Preferably, the collagen is sprayed onto the fibrous side of the serous membrane.

Also provided is a biocompatible collagen-coated serous membrane prepared by the above-described method.

The details of one or more embodiments of the invention are set forth in the description below. Other features, objects, and advantages of the invention will be apparent from the description and from the claims.

DETAILED DESCRIPTION

This invention relates to a method for preparing a tissue-based coated membrane resulting in a membrane that is smooth on both sides so as to minimize tissue adhesion.

The method for producing a smooth tissue-based coated membrane includes the following six key steps. First, the fibrous, i.e., parietal, side of an isolated tissue-based membrane is scraped to remove adhering fibers. Second, the tissue-based membrane is processed with an enzyme and chemicals to remove cells, lipids, and extractable blood and non-collagenous molecules. Third, the processed tissue-based membrane is freeze dried. Fourth, the fibrous side of the tissue-based membrane is compressed. Fifth, the compressed fibrous side of the tissue-based membrane is coated with collagen. Finally the collagen coated tissue-based membrane is exposed to a crosslinking agent.

Tissue-based membranes, e.g., bovine or porcine peritoneum or pericardium, provided by commercial suppliers generally contain fibers that adhere to the parietal side of the membrane, resulting from mechanical separation of the tissue-based membrane from neighboring tissues.

Depending on the location of the membrane in the body and the harvesting technique, the amount of adhering fibers varies. Removal of the adhering fibers is important to minimize potential surface irregularities. Applicants disclose that rinsing the membrane with a dehydrating agent, such as a low molecular weight organic compound or an alcohol, can facilitate the removal of adhering fibers, as partial dehydration renders the fibers stiff and more easily removed by scraping or other mechanical means. For example, the membrane can be rinsed with acetone, methanol, ethanol, or isopropanol.

The next step in processing the tissue-based membrane is to remove as much of the loosely associated proteins, cell debris, DNA materials, blood associated proteins, water soluble moieties, and lipids as possible using a combination of enzymes and chemicals. A series of sequential chemical treatments and treatment with an enzyme are performed to remove non-collagenous moieties from the tissue, to remove DNA molecules from cells and cell nuclei from the tissue, and to inactivate undesired potentially harmful viruses from the tissue. The chemicals and enzyme used for carrying out this step include 0.1-3% octylphenol ethoxylate (TRITON X-100™, 2-8 hour treatment), DNAse (2-18 hour treatment), 1 M NaOH (5-10 hour treatment), 0.5 M HCl (5-10 hour treatment), 1 M NaCl (24-48 hour treatment), isopropyl alcohol (24-72 hour treatment), and water (5-24 hour treatment).

The enzyme and chemical treatments described above remove most of the non-collagenous proteins, lipids, and cell-associated moieties from the tissue. Yet, the tissue retains its native structure and associated handling and mechanical properties.

The clean, treated tissue is then freeze-dried under conditions well known in the art, such as those disclosed in U.S. Pat. No. 6,391,333, the content of which is hereby incorporated by reference in its entirety. Typically, for thin membranes, freeze drying is accomplished by incubation of the membrane at −20° C. for 24-48 hours at a vacuum below 300 Torr, followed by drying at 20° C. for 8-24 hours.

After the above treatments, the freeze-dried membrane is still rough on its parietal, i.e., fibrous, side. In order to make the fibrous side smooth, it is coated with collagen. The membrane is prepared for coating in two steps. First, it is softened by incubation in a humidified chamber. Exposure of the membrane to a relative humidity greater than 90% for 1 to 4 hours is normally sufficient to soften the membrane for further processing. Second, the softened membrane is then compressed by passing a roller over the fibrous side of the membrane. The roller has sufficient weight to completely flatten and smooth any surface fibers still adhering to the fibrous side of the membrane. For example, the weight of the roller can be between 2 and 8 kg.

The coating of the membrane can be accomplished by spraying the surface with acid dispersed collagen fibers (e.g., dispersed in lactic acid) at a pH of 2.3-2.5, or alkaline dispersed collagen fibers (e.g., dispersed in NaOH) at a pH of 11 to 12. Any commercial sprayer (e.g., Badger Airbrush Model 150) can be used to spray the dispersed collagen fibers onto the fibrous side of the membrane. Spraying can be performed at 10-60 psi using a nozzle size of 0.1-1.0 mm. The concentration of collagen fibers in the spraying solution ranges from about 0.05% to about 0.1% (w/v) such that the collagen is sprayed in the form of a mist that coats the membrane surface uniformly despite any microscopic irregularities that may exist. A single layer or multiple layers of a collagen coating can be applied via this spraying technique. Typically, the thickness of the collagen coating is in the range of 5-50 μm.

Alternatively, the fibrous surface can be coated with an acid dispersed collagen using a brush. The concentration of collagen used for brush coating can be significantly higher than that used for spraying, ranging from about 0.1% to about 0.9% (w/v). The collagen coating applied using a brush is significantly thicker than that applied by spraying, ranging from about 50 μm to about 100 μm.

Further, the membrane can be dipped into a collagen dispersion in order to coat the fibrous surface of the membrane.

Irrespective of the collagen coating technique employed, the coated membrane is dried so as to more strongly integrate collagen with the membrane surface.

The coated membranes can be crosslinked using a crosslinking agent that is well known in the art. Crosslinking can be conducted in a solution containing a crosslinking agent (e.g., glutaraldehyde, formaldehyde) or by exposing the coated membrane to the vapor of a crosslinking agent (e.g., formaldehyde vapor). The extent of crosslinking in solution is a function of the concentration of the crosslinking agent, the temperature of the solution, and the time of crosslinking. For example, crosslinking can be accomplished by exposing the coated membrane to a 0.5% formaldehyde solution for 5 hours at room temperature. The crosslinking condition can significantly affect the characteristics of the membrane. For example, a high concentration of the crosslinking agent and a longer crosslinking time will result in a less conformable membrane having a slow rate of in vivo resorption. Conversely, in order to prepare a more conformable membrane, a low concentration of a crosslinking agent is preferred. The same principle applies to the vapor crosslinking, where a lower vapor pressure of a crosslinking agent will produce a more conformable membrane. The crosslinked membrane can be rinsed or exposed to air in order to reduce the amount of any crosslinking agent residue to a level that is acceptable for human implantation.

Without further elaboration, it is believed that the above description has adequately enabled the present invention. The following three examples are, therefore, to be construed as merely illustrative, and not limitative of the remainder of the disclosure in any way whatsoever.

EXAMPLES

Example 1

Collagen-Coated Bovine Pericardium Membrane

Preparation of Purified Tendon Collagen

The fat and fascia of a bovine flexor tendon were carefully removed and the tendon washed with water. The cleaned tendon was frozen and comminuted by slicing into 0.5 mm slices with a slicer. The sliced tendon was first extracted in purified water at room temperature for 24 hours. After decanting the water, a solution of 0.2 M HCl in 0.5 M $Na_2SO_4$ was added and the tendon slices were extracted at room temperature for 24 hours. The acid solution was neutralized by adding 3 M NaOH to raise the pH to approximately 7. The tendon slices were extracted in this first neutralized salt solution for 18 hours, after which the solution was removed by decanting. The acid-extracted tendon was then further extracted with 0.75 M NaOH in 1 M $Na_2SO_4$ at room temperature for 24 hours. This base solution was neutralized to a pH of approximately 7 by adding 3 M HCl. The tendon slices were extracted in this second neutralized salt solution for 18 hours, after which the solution was removed by decanting. After the two just-mentioned neutralized salt extractions, the tendon slices were rinsed with purified water 4 times in order to remove any residual salts. The extracted, rinsed tendon was then defatted with 99% isopropanol for 8 hours at room temperature. The isopropanol was decanted and a second equal volume of 99% isopropanol was added to further extract the tendon slices for 18 hours at room temperature.

All extraction steps described above were performed under constant agitation. Further, all extractions, with the exception of the isopropanol extractions, were performed using 5 ml of extracting solution per gram of tendon processed. The isopropanol extractions were performed using 3 ml of isopropanol per gram of tendon processed.

The defatted tendon was then dried under a clean air hood. The processed tendon material, consisting primarily of purified fibrillar collagen, was stored dry at room temperature for later use.

Preparation of Acid Dispersed Collagen Fibers

A 0.1% (w/v) acidic collagen dispersion was prepared by swelling 1 g of purified fibrillar collagen in one liter of 0.07 M Lactic acid at 4° C. in a refrigerator overnight. The swollen fibers were then homogenized for 60 seconds using a Silverson homogenizer and filtered through a 50 mesh stainless steel filter. The acidic dispersion was then stored in the refrigerator for later use.

Purification of Bovine Pericardium Membrane

Fat and extraneous tissue were mechanically removed from the raw bovine pericardium tissue and washed with water. The pre-cleaned bovine pericardium was first washed in purified water at room temperature for 2 hours. The water was decanted, 0.1% TRITON X-100™/DNase was added, and the pericardium was extracted for two hours at room temperature. The amount of DNase used was 4 units of activity per $cm^2$ of membrane. The solution was decanted and the bovine pericardium was then rinsed with purified water for 2 hours. The detergent/enzyme-extracted bovine pericardium was then defatted by incubation with 99% isopropanol three times for 6, 18, and 24 hours at room temperature. The defatted bovine pericardium was then extracted in 0.5 M HCl in 0.5 M $Na_2SO_4$ for 6 hours at room temperature. This acidic solution was neutralized by adding 3 M NaOH to a pH of approximately 7. The bovine pericardium was then extracted in the neutralized salt solution for 18 hours and the solution was decanted. The acid extracted bovine pericardium was then further extracted in 1 M NaOH in 1.2 M $Na_2SO_4$ at room temperature for 6 hours. This basic solution was neutralized by adding 3 M HCl to a pH of approximately 7. The bovine pericardium was then extracted in the neutralized salt solution for 18 hours and the solution was decanted. After the salt extractions, the bovine pericardium was washed 4 times with purified water to remove the residual salts associated with the purified bovine pericardium. All extraction steps were performed under constant agitation.

All extractions, with the exception of the isopropanol extractions, were performed using 3 ml of extracting solution per $cm^2$ of bovine pericardium processed. The isopropanol extractions were performed using 2.7 ml of isopropanol per $cm^2$ of bovine pericardium processed.

The purified bovine pericardium was then freeze-dried and stored until later use.

Coating of the Purified Bovine Pericardium with Acid Dispersed Collagen

The freeze-dried purified bovine pericardium was humidified in a humidification tank for approximately 30-60 minutes at a relative humidity of 90-100%. The fibrous (parietal) side of the membrane was then compressed using a roller under light pressure in a single uniform direction to flatten the fibers along that direction. The roller weighed 4 kg, and the light pressure was provided solely by the weight of the roller. The membrane was placed in a clean air hood to dry for a minimum of 15 minutes. The membrane was then placed in a holding frame and, using an air-brush gun (Badger Airbrush Model 150), the membrane was sprayed with a 0.1% (w/v) acidic collagen dispersion for 30 seconds. The collagen dispersion was sprayed at 40 psi through a 0.3 mm nozzle. The sprayed membrane was then placed into a glass dish and lightly crosslinked with a 0.001% glutaraldehyde solution for 3 hours. The crosslinked membrane was then rinsed with purified water and freeze-dried again.

Characterization of the Collagen-Coated Bovine Pericardium Membrane

Scanning electron microscopy (SEM) was performed on collagen-coated and non-coated samples at 50× magnification using a scanning electron microscope (JEOL Ltd. Model JSM 6100 SEM). The samples were mounted on an aluminum planchet using adhesive carbon tape. Approximately 500 angstroms of pure gold was sputtered onto the samples to improve electron beam conduction and prevent sample charging.

The fibrous (parietal) side of a bovine pericardial membrane has a rough appearance as visualized under SEM as a result of randomly-oriented fibers on the surface of the membrane. A smooth surface is seen under SEM after coating the parietal surface of the bovine pericardial membrane with collagen following the procedure described above. The smooth (visceral) non-coated side of the bovine pericardial membrane is similar in appearance to the coated fibrous side.

Example 2

Collagen-Coated Porcine Peritoneum Membrane

Fat and extraneous tissue were mechanically removed from the porcine peritoneum and washed with water. The pre-cleaned porcine peritoneum was first washed in purified water at room temperature for 2 hours. The water was decanted and 3% TRITON X-100™ was added to the peritoneum and incubated for 7 hours at room temperature. The TRITON X-100™ solution was decanted and the peritoneum then incubated in a DNase solution for 18 hours. The amount of DNase used was 8 units of activity per $cm^2$ of membrane. The detergent and enzyme extracted porcine peritoneum was defatted by incubating it with 99% isopropanol three times for 3, 3, 18, and 24 hours at room temperature. The defatted porcine peritoneum was extracted in 0.5 M HCl in 0.5 M $Na_2SO_4$ for 6 hours at room temperature. This acidic solution was neutralized using 3 M NaOH to a pH of approximately 7. The porcine peritoneum was further extracted in the neutralized salt solution for 18 hours and the solution was decanted. The acid extracted porcine peritoneum was then extracted in 1 M NaOH in 1.2 M $Na_2SO_4$ at room temperature for 6 hours. This basic solution was neutralized using 3 M HCl to a pH of approximately 7. The porcine peritoneum was further extracted in the neutralized salt solution for 18 hours and the solution was decanted. After the salt extractions, the porcine peritoneum was washed 4 times with purified water to remove the residual salts associated with the purified porcine peritoneum.

All extractions, with the exception of the isopropanol extractions, were performed using 3 ml of extracting solution per $cm^2$ of porcine peritoneum processed. The isopropanol extractions were performed using 2.7 ml of isopropanol per $cm^2$ of porcine peritoneum processed.

The purified porcine peritoneum was freeze-dried and stored until later use.

The purified porcine peritoneum membrane was coated with acid dispersed collagen as described above for the bovine pericardium membrane.

Example 3

Coating of Bovine Pericardium with Alkaline Dispersed Collagen Fibers

A 0.1% (w/v) alkaline collagen dispersion was prepared by swelling 1 g of fibrillar collagen purified as described above in one liter of 0.01 M NaOH at 4° C. in a refrigerator overnight. The swollen fibers were then homogenized for 90 seconds using a Silverson homogenizer, after which they were filtered through a 50 mesh stainless steel filter. The alkaline dispersion was then stored in the refrigerator for later use.

A bovine pericardium membrane is purified as described above. Alkaline dispersed collagen fibers are coated onto the purified membrane as described above for acid dispersed collagen fibers.

Example 4

Coating of Porcine Peritoneum With Alkaline Dispersed Collagen Fibers

A 0.1% (w/v) alkaline collagen dispersion was prepared by swelling 1 g of fibrillar collagen purified as described above in one liter of 0.01 M NaOH at 4° C. in a refrigerator overnight. The swollen fibers were then homogenized for 90 seconds using a Silverson homogenizer, after which they were filtered through a 50 mesh stainless steel filter. The alkaline dispersion was then stored in the refrigerator for later use.

A porcine peritoneum membrane is purified as described above. Alkaline dispersed collagen fibers are coated onto the purified membrane as described above for acid dispersed collagen fibers.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for preparing a biocompatible collagen-coated serous membrane, the method comprising:
   scraping a fibrous side of a serous membrane to remove adhering fibers;
   treating the serous membrane to remove cells, lipids, and extractable blood and non-collagenous molecules;
   freeze-drying the treated serous membrane;
   compressing the fibrous side of the serous membrane;
   coating the fibrous side of the serous membrane with a collagen; and
   exposing the collagen coated serous membrane to a crosslinking agent to effect crosslinking.

2. The method of claim 1, wherein the serous membrane is rinsed with a dehydrating agent prior to the scraping step.

3. The method of claim 2, wherein the dehydrating agent is an alcohol.

4. The method of claim 1, wherein the serous membrane is pericardium, peritoneum, amnion, small intestine submucosa, pleural, or vaginal tunics.

5. The method of claim 1, wherein the collagen is fiber-forming collagen.

6. The method of claim 5, wherein the fiber-forming collagen is type I collagen, type II collagen, type III collagen, or a combination thereof.

7. The method of claim 6, wherein the fiber-forming collagen is type I collagen.

8. The method of claim 1, wherein the coating is accomplished by spraying the collagen onto the fibrous side of the serous membrane.

9. The method of claim 1, wherein the coating is accomplished by brushing the collagen onto the fibrous side of the serous membrane.

10. The method of claim 1, wherein the coating is accomplished by dipping the fibrous side of the serous membrane into the collagen.

11. The method of claim 8, wherein the serous membrane is pericardium or peritoneum.

12. The method of claim 11, wherein the collagen is type I collagen.

* * * * *